US009295586B2

(12) United States Patent
Locke et al.

(10) Patent No.: US 9,295,586 B2
(45) Date of Patent: *Mar. 29, 2016

(54) ABSORBENT POLYMER DRESSINGS, SYSTEMS, AND METHODS EMPLOYING EVAPORATIVE DEVICES

(75) Inventors: Christopher Brian Locke, Bournemouth (GB); Timothy Mark Robinson, Basingstoke (GB); Richard Daniel John Coulthard, Verwood (GB)

(73) Assignee: KCI Licensing, Inc., San Antonio, TX (US)

( * ) Notice: Subject to any disclaimer, the term of this patent is extended or adjusted under 35 U.S.C. 154(b) by 1010 days.

This patent is subject to a terminal disclaimer.

(21) Appl. No.: 13/442,612

(22) Filed: Apr. 9, 2012

(65) Prior Publication Data

US 2013/0053799 A1 Feb. 28, 2013

Related U.S. Application Data

(60) Provisional application No. 61/529,735, filed on Aug. 31, 2011, provisional application No. 61/529,722, filed on Aug. 31, 2011, provisional application No. 61/529,709, filed on Aug. 31, 2011, provisional application No. 61/529,751, filed on Aug. 31, 2011.

(51) Int. Cl.
| | |
|---|---|
| *A61M 1/00* | (2006.01) |
| *A61F 13/00* | (2006.01) |
| *A61F 13/02* | (2006.01) |
| *A61M 27/00* | (2006.01) |
| *A61M 5/178* | (2006.01) |
| *A61M 5/00* | (2006.01) |

(Continued)

(52) U.S. Cl.
CPC ....... *A61F 13/00055* (2013.01); *A61F 13/0216* (2013.01); *A61M 1/009* (2014.02); *A61M 1/0058* (2013.01); *A61M 27/00* (2013.01); *Y10T 29/49826* (2015.01)

(58) Field of Classification Search
CPC ......... A61M 1/00; A61M 5/178; A61M 5/00; A61M 5/32; A61M 35/00; A61F 13/00
See application file for complete search history.

(56) References Cited

U.S. PATENT DOCUMENTS

| | | | |
|---|---|---|---|
| 1,355,846 A | 10/1920 | Rannells | |
| 2,052,869 A * | 9/1936 | Coanda | ......................... 239/418 |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.

(Continued)

*Primary Examiner* — Michele Kidwell
*Assistant Examiner* — Ilya Treyger

(57) ABSTRACT

Wound treatment systems and methods are presented that involve treating a wound, such as a burn wound, with an absorbent polymer that helps maintain a desired moisture level and that also involve an evaporative subsystem that removes excess liquid from the absorbent polymer. Other systems, methods, and dressings are presented herein.

10 Claims, 4 Drawing Sheets

(51) Int. Cl.
*A61M 5/32* (2006.01)
*A61M 35/00* (2006.01)

(56) References Cited

U.S. PATENT DOCUMENTS

| | | | |
|---|---|---|---|
| 2,547,758 A | 4/1951 | Kelling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 3,901,236 A * | 8/1975 | Assarsson et al. | 604/368 |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 8,795,257 B2 * | 8/2014 | Coulthard et al. | 604/541 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2010/0106079 A1 * | 4/2010 | Alimi | 604/24 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | WO 2011/130570 | * 10/2011 |

OTHER PUBLICATIONS

Susan Mendez-Eatmen, RN; "When wounds Wong Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philadelphia, PA, USA.

John Masters; "Reliable, Inexpensive and Simple Suction Dressings"; Letter to the Editor, British Journal of Plastic Surgery, 198, vol.

(56) References Cited

OTHER PUBLICATIONS 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Bjorn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinoviḉ, V. ?uki?, Ž. Maksimoviḉ, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

\* cited by examiner

ABSORBENT POLYMER DRESSINGS, SYSTEMS, AND METHODS EMPLOYING EVAPORATIVE DEVICES

RELATED APPLICATIONS

The present invention claims the benefit, under 35 USC §119(e), of the filings of U.S. Provisional Patent Application Ser. No. 61/529,735, entitled "ABSORBENT POLYMER DRESSINGS, SYSTEMS, AND METHODS EMPLOYING EVAPORATIVE DEVICES," filed 31 Aug. 2011, which is incorporated herein by reference for all purposes; U.S. Provisional Patent Application Ser. No. 61/529,722, entitled "REDUCED-PRESSURE DRESSINGS, SYSTEMS, AND METHODS WITH EVAPORATIVE DEVICES," filed on 31 Aug. 2011, which is incorporated herein by reference for all purposes; U.S. Provisional Patent Application Ser. No. 61/529,709, entitled "EVAPORATIVE FLUID POUCH AND SYSTEMS FOR USE WITH BODY FLUIDS," filed 31 Aug. 2011, which is incorporated herein by reference for all purposes; U.S. Provisional Patent Application Ser. No. 61/529,751, entitled "REDUCED-PRESSURE INTERFACES, SYSTEMS, AND METHODS EMPLOYING A COANDA DEVICE," filed on 31 Aug. 2011, which is incorporated herein by reference for all purposes; and U.S. patent application Ser. No. 13/084,813, entitled "DRESSINGS AND METHODS FOR TREATING A TISSUE SITE ON A PATIENT," filed on 12 Apr. 2011, which is incorporated herein by reference for all purposes.

FIELD

The present disclosure relates generally to medical treatment systems, and more particularly, but not by way of limitation, to absorbent polymer dressings, systems, and methods employing evaporative devices.

BACKGROUND

Managing fluids from a wound is given considerable attention in caring for many wounds. Some wounds, such as burns and grafts, require particular conditions to maximize healing. Efforts to present the right moisture balance for these types of wounds has proven difficult.

SUMMARY

According to an illustrative embodiment, a wound treatment system involves treating a wound, such as a burn wound, with an absorbent polymer that helps maintain a desired moisture level and also involves an evaporative subsystem that removes excess liquid from the absorbent polymer.

According another illustrative embodiment, a wound treatment system for treating a wound on a patient includes an absorbent polymer having a first side and a second, patient-facing side. The second, patient-facing side of the absorbent polymer is for disposing proximate to the wound. The wound treatment system further includes a first sealing member for covering the first side of the absorbent polymer and a portion of intact skin to form a sealed space in which the absorbent polymer is disposed. The first sealing member comprises a high-moisture vapor-transfer-rate member. The wound treatment system also includes an air-movement manifold disposed on the first sealing member, a second sealing member covering the air-movement manifold to form a channel space, and at least one port formed on the second sealing member for allowing the ingress or egress of air. The wound treatment system further includes a pressure source fluidly coupled to the air-movement manifold for producing an airflow in the air-movement manifold, a saturation sensor in communication with the absorbent polymer, and a controller operatively coupled to the pressure source for controlling the pressure source and operatively coupled to the saturation sensor. The controller and saturation sensor are operative to activate the pressure source to deliver air to the air-movement manifold when the absorbent polymer is saturated.

According to another illustrative embodiment, a method of treating a tissue site includes disposing an absorbent polymer proximate to the tissue site and covering the absorbent polymer and a portion of intact skin with a first sealing member to form a sealed space in which the absorbent polymer is disposed. The first sealing member comprises a high-moisture-vapor-transfer-rate member. The method also includes disposing an air-movement manifold on the first sealing member and covering the air-movement manifold with a second sealing member to form a channel space. The second sealing member has at least one port for allowing the ingress or egress of air. The method further includes fluidly coupling a pressure source to the air-movement manifold and activating the pressure source when the absorbent polymer is saturated to produce airflow in the air-movement manifold to create an enhanced humidity gradient across the first sealing member to facilitate liquid removal from the absorbent polymer. The step of activating the pressure source when the absorbent polymer is saturated may include disposing a saturation sensor at a location to measure the saturation of the absorbent polymer and operatively coupling a controller to the pressure source for controlling the pressure source and operatively coupling the controller to the saturation sensor. The controller is configured to monitor the saturation sensor and once detecting a threshold saturation to activate the pressure source.

According to another illustrative embodiment, a wound treatment system for treating a wound on a patient includes an absorbent polymer having a first side and a second, patient-facing side. The second, patient-facing side of the absorbent polymer is for disposing proximate to the wound. The wound treatment system further includes a wicking member having a first side and a second, patient-facing side. The second, patient-facing side of the wicking member is disposed proximate to the first side of the absorbent polymer. The wicking member is less hydrophilic than the absorbent polymer. The wound treatment system also includes a first sealing member for covering the first side of the wicking member and a portion of intact skin to form a sealed space in which the absorbent polymer and wicking member are disposed. The first sealing member comprises a high-moisture-vapor-transfer-rate member. The wound treatment system further includes an air-movement manifold disposed on the first sealing member, a second sealing member covering the air-movement manifold to form a channel space, and at least one port formed on the second sealing member for allowing the ingress or egress of air. The wound treatment system further includes a pressure source fluidly coupled to the air-movement manifold for producing an airflow in the air-movement manifold.

According to another illustrative embodiment, a method of treating a tissue site includes disposing an absorbent polymer proximate to the tissue site and disposing a wicking member on the absorbent polymer. The wicking member is less hydrophilic than the absorbent polymer. The method further includes covering the absorbent polymer, wicking member, and a portion of intact skin with a first sealing member to form a sealed space in which the absorbent polymer and wicking member are disposed. The first sealing member comprises a high-moisture-vapor-transfer-rate member. The method also includes disposing an air-movement manifold on the first sealing member and covering the air-movement manifold with a second sealing member to form a channel space. The second sealing member has at least one port for allowing the ingress or egress of air. The method also includes fluidly coupling a pressure source to the air-movement manifold and activating the pressure source to delivering air into the air-movement manifold.

According to another illustrative embodiment, a method of manufacturing a wound treatment system for treating a wound on a patient includes forming an absorbent polymer having a first side and a second, patient-facing side. The second, patient-facing side of the absorbent polymer is for disposing proximate to the wound. The method also includes forming a wicking member having a first side and a second, patient-facing side. The second, patient-facing side of the wicking member is disposed proximate to the first side of the absorbent polymer. The wicking member is formed to be less hydrophilic than the absorbent polymer. The method further includes providing a first sealing member. The first sealing member comprises a high-moisture-vapor-transfer-rate member. The methods also involve covering the first side of the wicking member with the first sealing member, providing an air-movement manifold, and disposing the air-movement manifold on the first sealing member over the wicking member, providing a second sealing member, and covering the air-movement manifold with the second sealing member to form a channel space. The method further includes forming at least one port formed on the second sealing member for allowing the ingress or egress of air and fluidly coupling a pressure source to the air-movement manifold for producing an airflow in the air-movement manifold.

Other aspects, features, and advantages of the illustrative embodiments will become apparent with reference to the drawings and detailed description that follow.

DETAILED DESCRIPTION OF ILLUSTRATIVE EMBODIMENTS

In the following detailed description of the illustrative, non-limiting embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is not to be taken in a limiting sense, and the scope of the illustrative embodiments are defined only by the appended claims.

Figure 1:
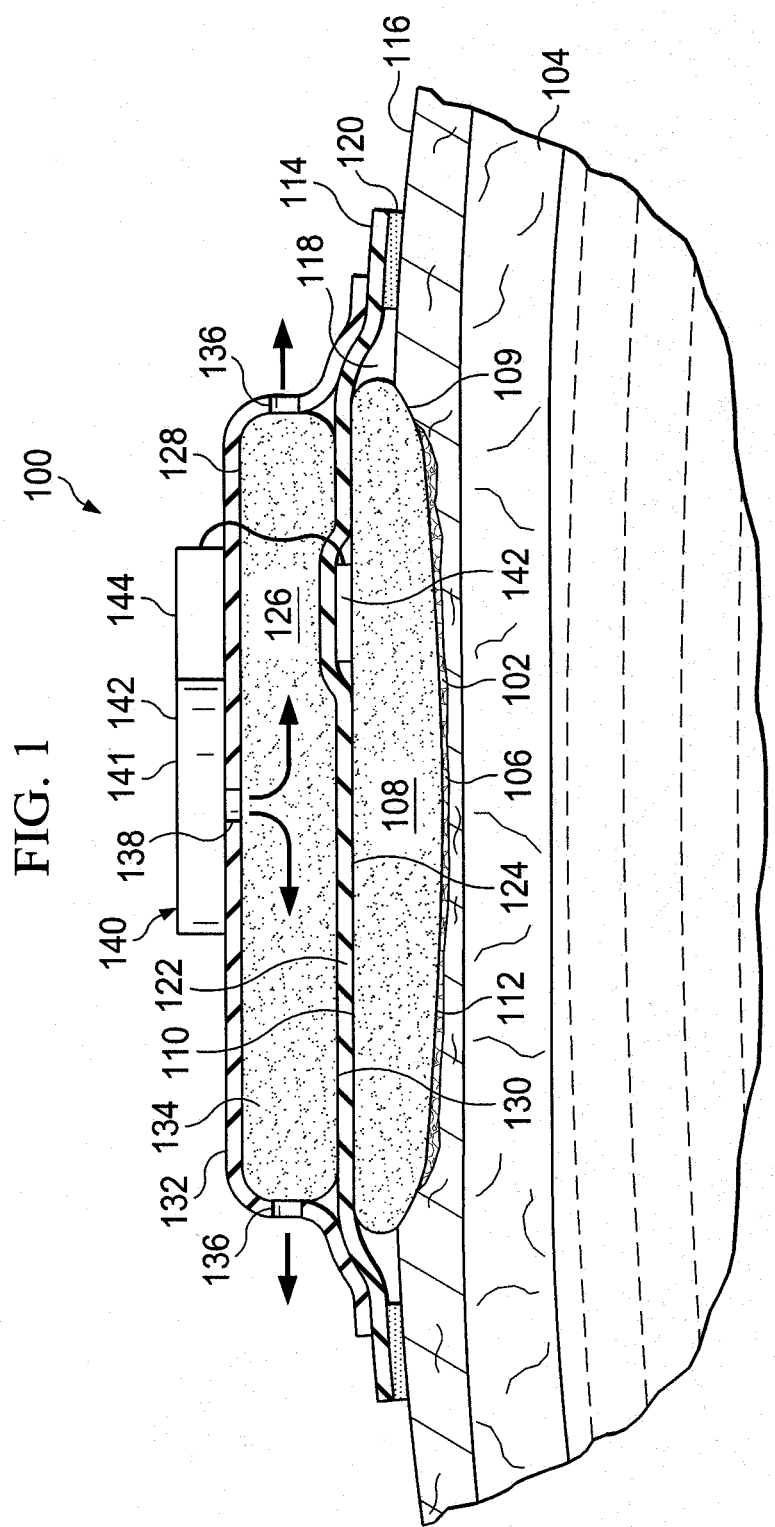
FIG. 1 is a schematic cross section of an illustrative embodiment of a wound treatment system for treating a wound on a patient.

Referring now to the drawings and primarily to FIG. 1, an illustrative embodiment of a wound treatment system 100 for treating a wound 102 on a patient 104 is presented. The wound treatment system 100 is particularly well suited for treating wounds that are sensitive to fluid, such as burns and grafts. For illustration purposes, the wound 102 is shown at the epithelialization stage of healing having already formed granulation tissue 106. The wound treatment system 100 maintains the desired moisture on the granulation tissue 106, presents a smooth surface, and efficiently processes the liquids produced by the wound 102.

The wound treatment system 100 includes an absorbent polymer 108 having a first side 110 and a second, patient-facing side 112. The second, patient-facing side 112 of the absorbent polymer 108 is for disposing proximate to the wound 102. The absorbent polymer 108 may be a hydrogel, hydrocolloid, small-celled hydrophilic foam, or other absorbent polymer. The absorbent polymer 108 may be selected for its absorbent quality and for its ability to bio-mimic. The absorbent polymer 108 may overlap the wound edge 109.

A first sealing member 114 covers the first side 110 of the absorbent polymer 108 and typically a portion of intact skin 116. The first sealing member 114 alone or with the second sealing member 132 form a sealed space 118. The absorbent polymer 108 is disposed in the sealed space 118. At least a portion of the first sealing member 114 may be releasably attached to the intact skin 116 by an attachment device 120, e.g., a medically acceptable, pressure-sensitive adhesive that extends about a periphery, a portion, or the entire first sealing member 114; a double-sided drape tape; paste; hydrocolloid; hydrogel; or other sealing devices or elements. The first sealing member 122 has a first side and a second, patient-facing side 124.

The first sealing member 114 comprises a high-moisture-vapor-transfer-rate member. The "Moisture Vapor Transmission Rate" or "MVTR" represents the amount of moisture that can pass through a material in a given period of time. The high-moisture-vapor-transfer-rate member allows vapor to egress from the sealed space 118 but not liquids. The high-moisture-vapor-transfer-rate member may comprise any of numerous materials, such as any of the following: hydrophilic polyurethane, cellulosics including cellulose esters, hydrophilic polyamides, hydrophilic acrylics, hydrophilic silicone polymers, polyvinyl alcohol and copolymers with polyvinyl acetate. As one specific, illustrative, non-limiting embodiment, the high-moisture-vapor-transfer-rate member may be formed from a breathable cast matt polyurethane film sold under the name INSPIRE 2301 from Expopack Advanced Coatings of Wrexham, United Kingdom. This illustrative film has a MVTR (inverted cup technique) of 14500-14600 g/m$^2$/24 hours. See www.exopackadvancedcoatings.com. The first sealing member 114, which is the high-moisture-vapor-transfer-rate member, may have various thicknesses, such as 10 to 40 microns (μm), e.g., 15, 20, 25, 30, 35, 40 microns or any number in the stated range.

An air-movement manifold 126 disposed on the first side 122 of the first sealing member 114. The air-movement manifold 126 has a first side 128 and a second, patient-facing side 130. The air-movement manifold 126 provides open pathways for airflow even when under compression developed by the wound treatment system 100. The air-movement manifold 126 may be any substance that carries out these functions. The air-movement manifold 126 may be, for example, one or more of the following: open cell foam, non-wovens such as Libeltex TDL2, woven fabrics including 3D or spacer fabrics (Baltex, Ilkeston, Derby, UK), or other suitable material.

A second sealing member 132 covers the air-movement manifold 126 and forms a channel space 134 in which the air-movement manifold 126 is disposed. The second sealing member 132 may be formed from the same materials as the first sealing member 114 or may be formed from other materials that adequately control air transmission. The second sealing member 132 has at least one port 136 formed on the second sealing member 132 for allowing the ingress or egress of air. More typically, a plurality of ports 136 are formed on the second sealing member 132. The ports 136 may be covered with a bacteria filter. An aperture 138 is formed through the second sealing member 132 to allow the ingress or egress of fluid.

The first sealing member 114 may be adhered to the intact skin 116 by an attachment device 120, e.g., an adhesive, and to the first side 110 of the absorbent polymer 108 and intact skin 116. The performance of the first sealing member 114 with respect to MVTR may be enhanced by only covering a limited surface area of the second, patient-facing side 124 of the first sealing member 114 with the attachment device 120. For example, only the peripheral edge of the first sealing member 114 may be covered or a limited pattern may be used. In the latter situation, according to one illustrative embodiment, only 30 to 60 percent of the surface area is covered with the attachment device 120. The limited coverage by the attachment device 120 on the second, patient-facing side 124 may be accomplished by applying the attachment device 120 in a pattern, e.g., grid, spaced dots, swirls, or other patterns. In another embodiment, the first sealing member 114 may be coupled by welding (e.g., ultrasonic or RF welding), bonding, stitching, staples, or another coupling device to the first side 110 of the absorbent polymer 108. The attachment device 120 may be applied only to a peripheral portion of the first sealing member 114.

An attachment device (not explicitly shown) may be used to couple the sealing member 132 to the first side 128 of the air-movement manifold 126 or first side 122 of the first sealing member 114. Analogous comments to those in the previous paragraph related to the first sealing member 114 apply for coupling the second sealing member 132 to the first side 128 of the air-movement manifold 126 or first side 122 of the first sealing member 114. In other embodiments, an attachment device may be disposed only on the peripheral edge of the second sealing member 132 or another coupling technique used.

A pressure source 140 or air mover is fluidly coupled to the air-movement manifold 126 for producing an airflow in the air-movement manifold 126. The pressure source 140 may be from a remote source delivered by a conduit (not shown) or a micro-pump 141 as shown. The pressure source 140 may be any device for supplying a reduced pressure or positive pressure, such as a vacuum pump, wall suction, micro-pump, Coanda device, or other source. For example, the pressure source 140 may be a piezoelectric micro-pump, such as the one shown in United States Patent Publication 2009/0240185 (application Ser. No. 12/398,904; filed 5 Mar. 2009), entitled, "Dressing and Method for Applying Reduced Pressure To and Collecting And Storing Fluid from a Tissue Site," which is incorporated herein for all purposes. The pressure source 140 may be configured to pull air from the aperture 138 or push air into the aperture 138. If the pressure source 140 provides reduced pressure, air will be pulled through the ports 136 and into the air-movement manifold 126 and ultimately to the pressure source 140. If the pressure source 140 provides positive pressure, air will be pushed into the aperture 138, through the air-movement manifold 126 and out of the ports 136.

A saturation sensor 142 is in operative communication with the absorbent polymer 108 and is typically on a portion of the absorbent polymer 108 as shown. The saturation sensor 142 is operatively coupled to a controller 144. The saturation sensor 142 may be any device that allows for monitoring of the saturation of the absorbent polymer 108. For example, without limitation, the saturation sensor 142 may be a resistive element that changes resistance when liquid covers the sensor, a galvanic cell that creates a voltage when covered with liquid from a wound or delivered from an instillation device, or a capacitance sensor that changes properties when liquids are nearby.

The controller 144 is operatively coupled to the pressure source 140 for controlling the pressure source 140 and operatively coupled to the saturation sensor 142. The controller 144 and saturation sensor 142 are operative to activate the pressure source 140 to deliver air to the air-movement manifold 126 when the absorbent polymer 108 is saturated. Saturated typically implies wet beyond a threshold or designed amount. The controller 144 and saturation sensor 142 are further operative to deactivate the pressure source 140 to cease delivery of air to the air-movement manifold 126 when the absorbent polymer 108 is no longer saturated.

In operation, according to one illustrative embodiment, the absorbent polymer 108 is disposed proximate to the wound 102 or tissue site. The absorbent polymer 108 and a portion of intact skin 116 are covered with the first sealing member 114 to form the sealed space 118 in which the absorbent polymer 108 is disposed. The air-movement manifold 126 is disposed on the first side 122 of the first sealing member 114. The air-movement manifold 126 is covered with the second sealing member 132 to form the channel space 134. The pressure source 140 is fluidly coupled to the air-movement manifold 126 through aperture 138. The pressure source 140 is activated to create an airflow in the air-movement manifold 126 to create a strong or enhanced relative humidity gradient across the first sealing member 114 that helps remove liquid or moisture from the absorbent polymer 108.

In this embodiment, the pressure source 140 is not activated until the absorbent polymer 108 is saturated as determined by the saturation sensor 142 and controller 144. Likewise, the saturation sensor 142 and controller 144 may be configured to determine when the absorbent polymer 108 is no longer saturated and in response to deactivate the pressure source 140. This active control keeps the absorbent polymer 108 at a balanced moisture equilibrium.

It should be noted that while the pressure source 140 and aperture 138 are shown in a central portion of the second sealing member 132, the pressure source 140 may be located at any location on the second sealing member 132. Typically, it will be desirable to maximize the distance between the pressure source 140 and the one or more ports 136.

Figure 3:
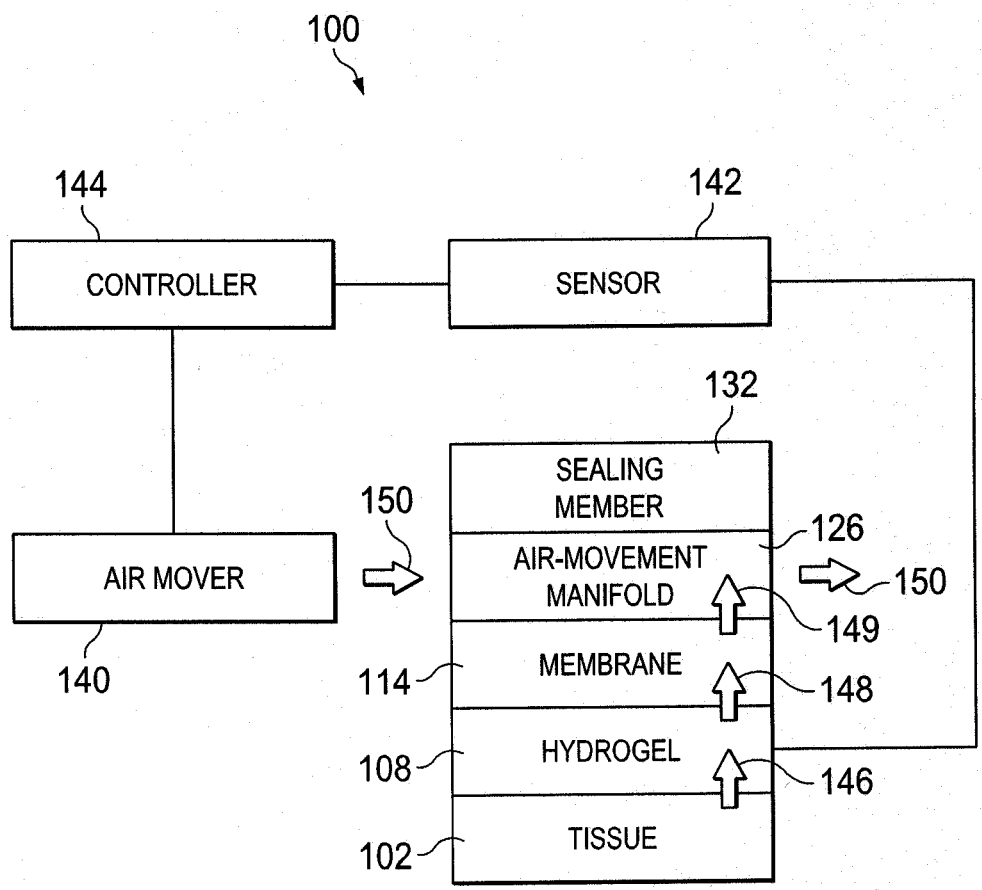
FIG. 3 is a schematic diagram of a wound treatment system for treating a wound on a patient.

Referring now primarily to FIG. 3, the operation of aspects of wound treatment system 100 will be further explained. The absorbent polymer 108, e.g., a hydrogel, is disposed proximate to the tissue or wound 102. Exudate or other fluids are given off as suggested by arrow 146 and are absorbed by the absorbent polymer 108. As the absorbent polymer 108 exceeds its designed moisture equilibrium, moisture is given off as suggested by arrow 148. The moisture is transmitted or diffused through first sealing member 114, or membrane, as suggested by arrow 149. Air moving (assuming the air mover or pressure source 140 is activated) in the air-movement manifold 126 carries off the moisture that is against the first sealing member 114. The moisture is transported out of the system 110 as suggested by arrows 150. The second sealing member 132 helps direct air from the pressure source 140 and in some embodiments may allow the egress of moisture as well directly across the second sealing member 132.

Figure 4:
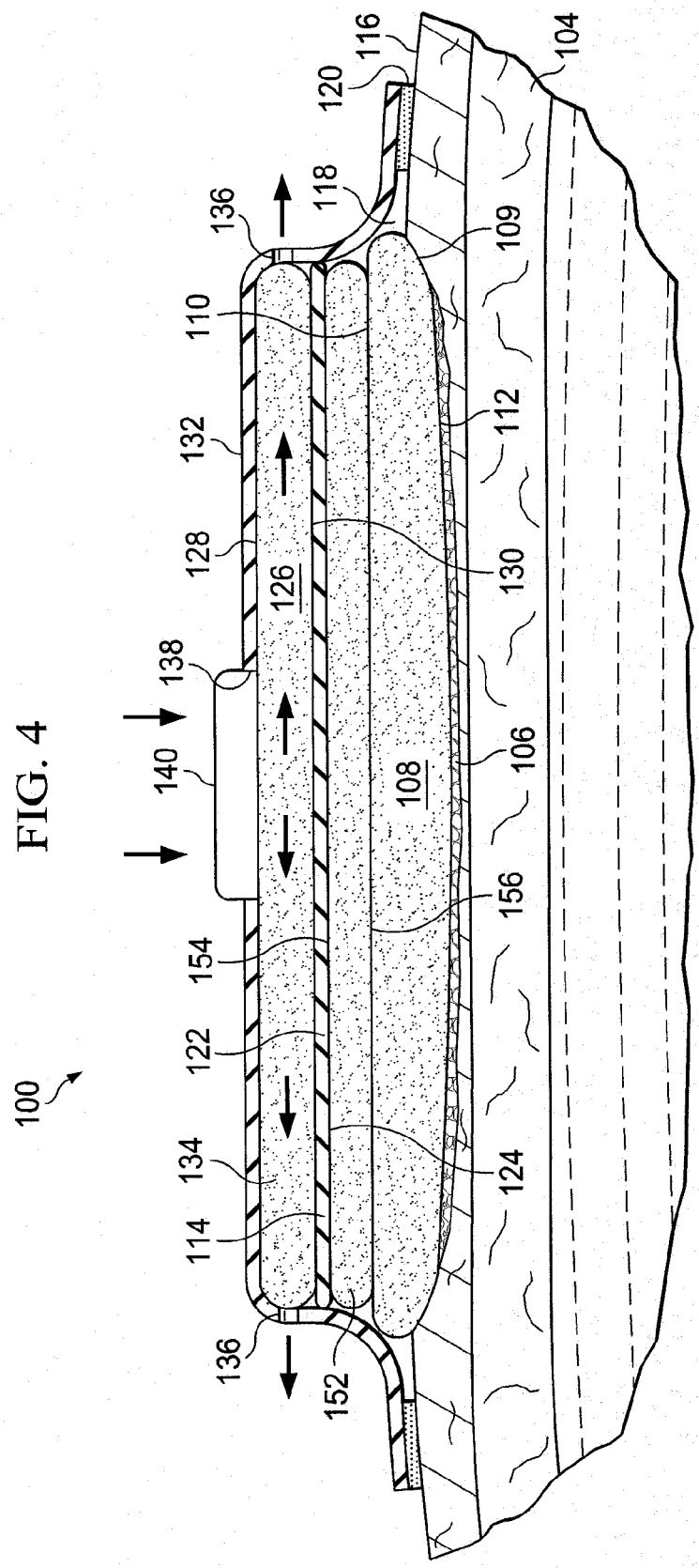
FIG. 4 is a schematic cross section of an illustrative embodiment of a wound treatment system for treating a wound on a patient.

Referring now primarily to FIG. 4, another illustrative embodiment of a wound treatment system 100 for treating a wound 102 on a patient 104 is presented. The wound treatment system 100 is analogous in many respects to the wound treatment system 100 of FIG. 1, and accordingly, some parts are labeled but not further discussed. The wound treatment system 100 of FIG. 4 differs primarily in that the embodiment does not have active control components (e.g., controller 144 and saturation sensor 142), but nonetheless regulates the moisture of the absorbent polymer 108. In addition, this embodiment includes a wicking member 152.

The wicking member 152 has a first side 154 and a second, patient-facing side 156. The second, patient-facing side 156 of the wicking member 152 is disposed proximate to the first side 110 of the absorbent polymer 108. The wicking member 152 may comprise one or more of the following: non woven such as Libeltex TDL2, or a woven fabric, or a hydrophilic porous member, such as an open celled foam. The wicking member 152 is less hydrophilic than the absorbent polymer 108. The wicking member 152 may be treated to increase or decrease the hydrophilicity of the wicking member 152 relative to the absorbent polymer 108. Treatments may include plasma, corona, coating or other methods of modifying the properties of the wicking member 152. Plasma and corona can be used to add polar groups (oxidation) to the surface to increase hydrophilicity. Furthermore, plasma treatments may incorporate active gases that are chemically bound to the treated surface, for example binding a hydrophilic polymer to the treated surface.

The first sealing member 114 covers the first side 154 of the wicking member 152 and alone or with the second sealing member 132 forms a sealed space 118 in which the absorbent polymer 108 and wicking member 152 are disposed. As in the previous embodiments, the first sealing member 114 comprises a high-moisture-vapor-transfer-rate member.

The pressure source 140 may be activated continuously or intermittently. In addition, in another illustrative embodiment, the active control components of FIG. 3 may also be applied to the wound treatment system 100 of FIG. 4 and the pressure source 140 actively controlled.

Figure 2:
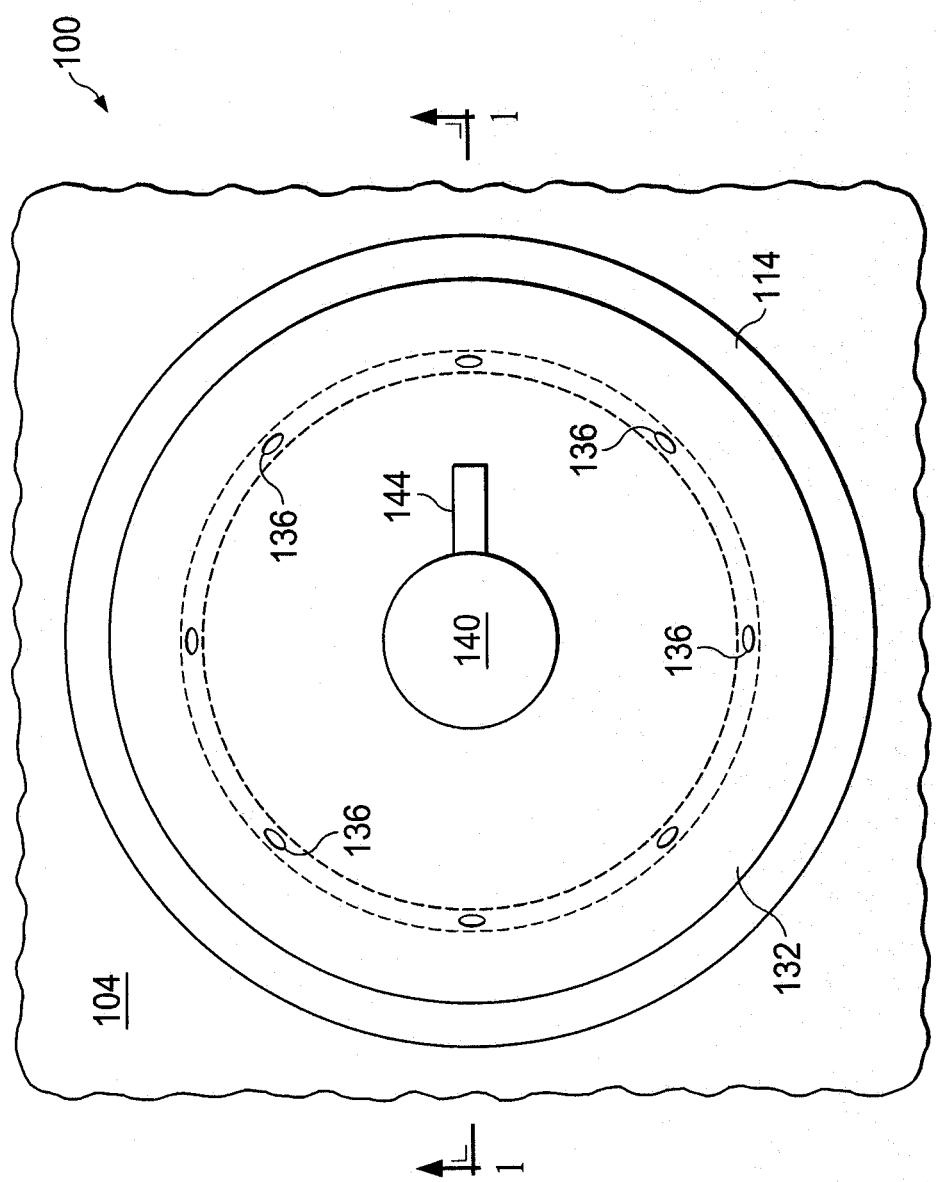
FIG. 2 is a schematic, plan view of the wound treatment system of FIG. 1.

In operation according to one embodiment, the system 100 is deployed in a manner analogous to the system 100 of FIGS. 1-2. The wound 102 exudes into the absorbent polymer 108. The absorbent polymer 108 absorbs the exudate, which includes liquids, and will eventually saturate the absorbent polymer 108. As the absorbent polymer 108 becomes saturated, the absorbent polymer 108 will begin to be transfer liquid to the wicking member 152, which has been selected or created to be less hydrophilic than the absorbent polymer 108. As such, the wicking member 152 will only take the liquids that the absorbent polymer 108 cannot incorporate. Once the wicking member 152 is also saturated, the fluid will begin to diffuse through the first sealing member 114 where the water molecules will be collected on the boundary layer of the first sealing member 114 and on the air-movement manifold 126. The fluid will be evaporated at a rate linked to the surface area of the first sealing member 114. The evaporation rate may be on the order of 3-4 ml/hour. When the fluid balance of the absorbent polymer 108 has been adequately reduced, there will no longer be a transfer of fluids to the wicking member 152.

In other words, the diffusion through the first sealing member 114 will slow until the available fluids on the wicking member 152 have reached a balance with the fluids on the boundary layer of the first sealing member 114, i.e., the wicking member 152 is adequately dry. At this time, due to the fact that the absorbent polymer 108 is more hydrophilic than the wicking member 152, the remaining fluids at the correct balance level will be retained by the absorbent polymer 108 and not transported to the wicking member 152 unless the wound 102 once more produces more than the absorbent polymer 108 can absorb, in which case the transport process will start again.

With all the embodiments herein that involve active control, additives may added to the absorbent polymer 108 such that the saturation sensor 142 may more easily detect saturation. For example, without limitation, a salt may be added to the absorbent polymer 108 that will assist with detection of changes in the electrical properties of the saturation sensor 142. In addition, the absorbent polymer 108 may be formulated with additives that act as humectants, such as glycerine and polyethylene glycols, which will not permit the absorbent polymer 108 to fully dry out.

While the wound treatment systems 100 are presented in the context of wounds 102, it should be understood that the liquid processing presented herein may also be used with other body fluids. For example, the wound treatment systems 100 may be used with urine.

The embodiments herein offer a number of perceived advantages. A few examples follows. The wound treatment systems 100 may be readily used with low severity, high liquid wounds. In addition, the wound treatment systems 100 allow more liquid to processed than would otherwise be possible. At the same time, the wound treatment system 100 will not dry out the absorbent polymer 108. The wound treatment system 100 may be able to stay in place longer than other dressing and thereby require fewer changes.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A wound treatment system for treating a wound on a patient, the wound treatment system comprising:
   an absorbent polymer having a first side and a second, patient-facing side, wherein the second, patient-facing side of the absorbent polymer is for disposing proximate to the wound;
   a first sealing member for covering the first side of the absorbent polymer and a portion of intact skin to form a sealed space in which the absorbent polymer is disposed, wherein the first sealing member comprises a high-moisture-vapor-transfer-rate member;
   an air-movement manifold disposed on the first sealing member;
   a second sealing member covering the air-movement manifold to form a channel space;
   at least one port formed on the second sealing member for allowing the ingress or egress of air;
   a pressure source fluidly coupled to the air-movement manifold for producing an airflow in the air-movement manifold, the pressure source comprising a Coanda device coupled to the second sealing member;
   a saturation sensor in communication with the absorbent polymer;
   a controller operatively coupled to the pressure source for controlling the pressure source and operatively coupled to the saturation sensor; and
   wherein the controller and saturation sensor are operative to activate the pressure source to deliver air to the air-movement manifold when the absorbent polymer is saturated.

2. The wound treatment system of claim 1, wherein the controller and saturation sensor are further operative to deactivate the pressure source to cease delivery of air to the air-movement manifold when the absorbent polymer is no longer saturated.

3. The wound treatment system of claim 1, wherein the absorbent polymer comprises a material selected from hydrogel and a hydrocolloid.

4. The wound treatment system of claim 1, wherein the saturation sensor comprises one or more resistive members that are monitoring for change in resistance.

5. The wound treatment system of claim 1, wherein the saturation sensor comprises a galvanic cell.

6. The wound treatment system of claim 1, wherein the pressure source comprises a micro-pump coupled to the second sealing member.

7. The wound treatment system of claim 1, wherein the Coanda device is fluidly coupled to a pressure conduit.

8. A method of manufacturing a wound treatment system for treating a wound on a patient, the method comprising:
   forming an absorbent polymer having a first side and a second, patient-facing side, wherein the second, patient-facing side of the absorbent polymer is for disposing proximate to the wound;
   forming a wicking member having a first side and a second, patient-facing side, wherein the second, patient-facing side of the wicking member is disposed proximate to the first side of the absorbent polymer, wherein the wicking member is formed to be less hydrophilic than the absorbent polymer, and wherein forming the wicking member comprises providing a wicking member and treating the wicking member to adjust the hydrophilicity to be less than the hydrophilicity of the absorbent polymer;
   providing a first sealing member, wherein the first sealing member comprises a high-moisture-vapor-transfer-rate member;
   covering the first side of the wicking member with the first sealing member;
   providing an air-movement manifold;
   disposing the air-movement manifold on the first sealing member over the wicking member;
   providing a second sealing member;
   covering the air-movement manifold with the second sealing member to form a channel space;
   forming at least one port formed on the second sealing member for allowing the ingress or egress of air; and
   fluidly coupling a pressure source to the air-movement manifold for producing an airflow in the air-movement manifold.

9. The method of claim 8, wherein the step of treating the wicking member comprises treating the wicking member with a plasma treatment.

10. The method of claim 8, wherein the step of treating the wicking member comprises treating the wicking member with a corona treatment.

* * * * *